US009305246B2

(12) United States Patent
Remer

(10) Patent No.: US 9,305,246 B2
(45) Date of Patent: Apr. 5, 2016

(54) METHOD OF ANALYZING TAMPER EVIDENT TAPE RESIDUE

(71) Applicant: U.S. Department of Homeland Security, Washington, DC (US)

(72) Inventor: James H. Remer, Atlantic City, NJ (US)

(73) Assignee: The United States of America, as Represented by the Secretary of Homeland Security, Washington, DC (US)

(*) Notice: Subject to any disclaimer, the term of this patent is extended or adjusted under 35 U.S.C. 154(b) by 105 days.

(21) Appl. No.: 13/965,280

(22) Filed: Aug. 13, 2013

(65) Prior Publication Data

US 2014/0099024 A1    Apr. 10, 2014

Related U.S. Application Data

(60) Provisional application No. 61/710,147, filed on Oct. 5, 2012.

(51) Int. Cl.
| | |
|---|---|
| *G06K 9/00* | (2006.01) |
| *G06K 9/78* | (2006.01) |
| *G06T 7/00* | (2006.01) |
| *G06K 9/64* | (2006.01) |
| *G06K 9/34* | (2006.01) |
| *G01N 1/02* | (2006.01) |
| *G01N 1/00* | (2006.01) |

(52) U.S. Cl.
CPC .. *G06K 9/78* (2013.01); *G01N 1/02* (2013.01); *G06K 9/34* (2013.01); *G06K 9/64* (2013.01); *G06T 7/0002* (2013.01); *G01N 2001/007* (2013.01); *G01N 2001/028* (2013.01)

(58) Field of Classification Search
None
See application file for complete search history.

(56) References Cited

U.S. PATENT DOCUMENTS

| | | | |
|---|---|---|---|
| 3,935,960 | A | 2/1976 | Cornell |
| 5,460,880 | A | 10/1995 | Patnode et al. |
| 5,673,586 | A | 10/1997 | Mann |
| 6,096,387 | A | 8/2000 | Decker |
| 6,715,820 | B1 | 4/2004 | Haas |
| 7,259,357 | B2 | 8/2007 | Walker |
| 7,913,552 | B2 | 3/2011 | Himmelbauer et al. |

(Continued)

FOREIGN PATENT DOCUMENTS

| | | |
|---|---|---|
| WO | 86/03472 A1 | 6/1986 |
| WO | 2009/122424 A1 | 10/2009 |

OTHER PUBLICATIONS

Rao, Ed. "Cargo supply chain technology development and standardization initiatives." Security Technology (ICCST), 2011 IEEE International Carnahan Conference on. IEEE, 2011.*

(Continued)

*Primary Examiner* — Li Liu
(74) *Attorney, Agent, or Firm* — Layanya Ratnam; Nathan Grebasch; William Washington

(57) ABSTRACT

Methods and systems for measuring the effectiveness of pigment transfer in a tamper evident tape. A test area can be established on a substrate upon which a residual image is formed by pulling a tamper-evident tape. The test area is divided into a predefined number of units. Then, the number of units in which a residual is left behind on a surface of the substrate can be counted and compared to the number of units within an area of un-applied tamper-evident tape of identical application design such that a percentage of units remaining on the substrate after removal of the tamper-evident tape with the residual comprises a criterion for evaluating a relative effectiveness of the tamper-evident tape.

17 Claims, 5 Drawing Sheets

(56) References Cited

U.S. PATENT DOCUMENTS

| 7,995,196 B1* | 8/2011 | Fraser | 356/71 |
| 2008/0078492 A1* | 4/2008 | D'Amato | 156/60 |
| 2010/0043694 A1* | 2/2010 | Patel | 116/201 |
| 2011/0020641 A1 | 1/2011 | Shroff et al. | |

OTHER PUBLICATIONS

ASTM D3330/D3330M-04(2010) Standard Test Method for Peel Adhesion of Pressure-Sensitive Tape http://www.astm.org/Standards/D3330.htm , printed Nov. 2, 2012, 3 pages.

Elias, B., "Screening and Securing Air Cargo: Background and Issues for Congress," Congressional Research Service Dec. 2, 2010, CRS Report for Congress, 21 pages.

Iyer, B. H. et al., "Need for Increased Security in Aviation in the Cargo Sector," Third Annual International Conference on Law & Regulation of Air Transport and Space Applications, created Jan. 14, 2012, National Law University, Delhi, 21 pages.

E. Rao, IEEE Xplore Abstract for "Cargo supply chain technology development and standardization initiatives", IEEE International Carnahan Conference on Security Technology (ICCST), Oct. 18-21, 2011, p. 1-2.

* cited by examiner

METHOD OF ANALYZING TAMPER EVIDENT TAPE RESIDUE

TECHNICAL FIELD

Embodiments are generally related to security alerting devices and techniques. Embodiments are also related to tamper-evident tape including, for example, self-adhesive resealable tape for promoting the security of packages or containers such as cargo pallets, boxes, bags, pouches, and the like. Embodiments also relate to the analysis and measurement of residue left behind by tamper-evident tape.

BACKGROUND OF THE INVENTION

Package security is a major concern of purveyors, shippers, and consumers of all types of products. Packages are frequently opened and their contents removed while in transit, in storage, or even on the store shelf. Packages whose security has been violated are often resealed to avoid suspicion and remove any outward evidence of tampering or pilferage. In consequence, it is difficult to determine where in the chain of distribution the theft or tampering occurred. Tamper-evident tapes enable manufacturers, shippers, and retailers to determine where the breach occurred and take appropriate measures to root out the person or persons responsible. Tamper-evident tape is also valued by consumers of food stuffs or other products wrapped in bags or pouches for it provides assurance that the product was not opened or adulterated prior to purchase.

Due to congressional action requiring 100% screening of all cargo moving on passenger aircraft, the U.S. Transportation Safety Administration (TSA) has explored various options for securing cargo and other items. The TSA and other organizations are constantly developing new systems, devices, and techniques for securing cargo. Tamper-evident tape may offer such a solution. One of the problems with existing tapes is that they are found to fail in many transportation security applications. Most existing tamper-evident tapes also leave very little image or residue and some simply fall off the target cargo (i.e., adhesion does not work). An effort was therefore made to standardize and treat potential strength such as ensuring that adhesion is sufficient for such tapes to remain on target cargo and other items.

Experiments and additional research have been conducted regarding to provide tests and standardization for tamper-evidence tapes to satisfy ISA performance standards. Industry standards for most physical properties of such tapes (e.g., adhesion, tensile strength, etc.) have been developed. However, additional work remains regarding analyzing patterns and residue left behind from such tapes, as will be explained It is well known that a high percentage of tamper-evident tape is damaged during transport and that tamper-evident tape and/or associated labels do not sufficiently seal consolidated cargo. Additionally, from an operational perspective, such tamper-evident tape and labels are extremely time-consuming to apply. From a detection perspective, it is generally difficult to identify a manipulated or damaged tamper-evident tape. Additionally, residue left by tamper-evident tapes and labels preclude use to seal reusable containers.

Tamper-evident tapes that leave behind a pigmented or physical residue when removed provide a relatively inexpensive and low weight way to secure cargo and other kinds of packages and contains. Purchases of such tapes may involve a large cost investment based on the amount of goods required to be secured. Although several kinds of tamper-evident tapes are available commercially, there is no government or industry standard that suggests an optimal amount of pigment transferred by the tamper-evident tape, and the effectiveness of the transfer, as well as manufacturer's claim, vary widely.

Several devices have been discussed for measuring the adhesion of tapes, but these do not measure the transfer of pigment. See, for example, U.S. Pat. No. 7,913,552 and U.S. Pat. No. 5,673,586, which are incorporated herein by reference. In addition, some existing devices for measuring adhesion require components that are based on the measurement of a physical force. None of these approaches and/or devices employs a visual or pattern analysis approach. It is therefore believed that a need exists for an objective measure of the effectiveness of the pigment transfer in tamper-evident tapes for use in security situations such as TSA applications.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the disclosed embodiments to provide for a visual analysis of the amount or residue transferred by a tamper-evident tape to a substrate after removal of the tamper-evident tape.

It is another aspect of the disclosed embodiments to provide for an objective measurement of the effectiveness of the pigment transfer in tamper-evident tapes.

It is another aspect of the disclosed embodiments to allow any tamper-evident tape manufacturer to demonstrate the effectiveness of their product relative to any regulatory requirements, industry recommendations or procurement requirements.

It is yet another aspect of the disclosed embodiments to implement methods and systems for establishing a standard of security.

The aforementioned aspects and other objectives and advantages can now be achieved as described herein. Methods and systems are disclosed for measuring the effectiveness of pigment transfer in a tamper evident tape. A test area can be established on a substrate upon which a residual image is formed by pulling a tamper-evident tape. The test area is divided into a predefined number of units. Then, the number of units in which a residual is left behind on a surface of the substrate can be counted and compared to the number of units within an area of un-applied tamper-evident tape of identical application design such that a percentage of units remaining on the substrate after removal of the tamper-evident tape with the residual comprises a criterion for evaluating a relative effectiveness of the tamper-evident tap

BRIEF DESCRIPTION OF THE DRAWINGS

The accompanying figures, in which like reference numerals refer to identical or functionally similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended, to limit the scope thereof.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1:
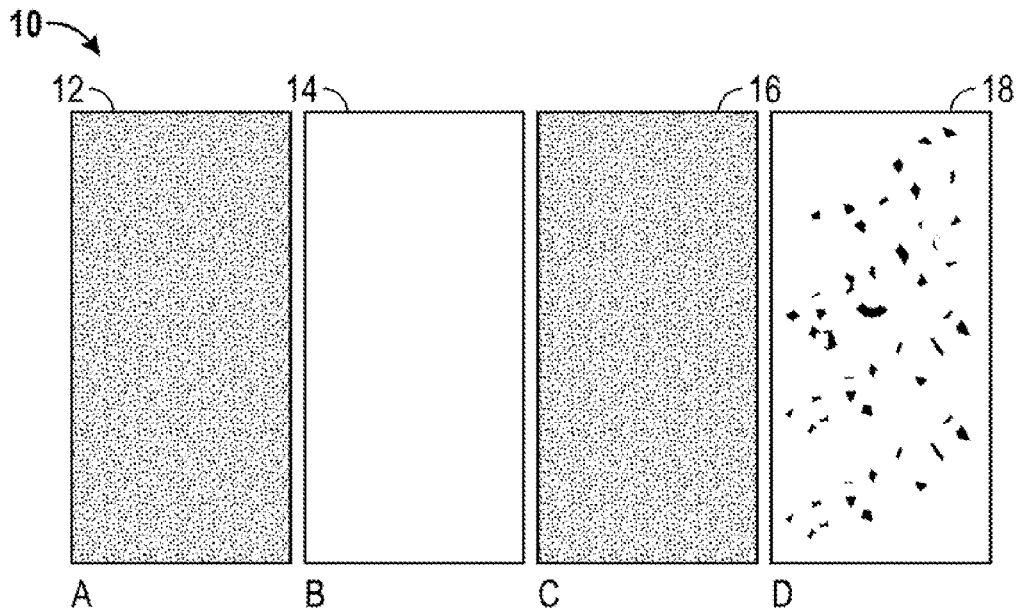
FIG. 1 illustrates a schematic diagram depicting tamper-evident tape performance, in accordance with a preferred embodiment.

FIG. 1 illustrates a schematic diagram 10 depicting tamper-evident tape performance, in accordance with a preferred embodiment. FIG. 1 generally depicts an original tamper-evident tape 12 on a substrate and an image on tamper-evident tape backing 14 after tape removal if optimal adhesion to the substrate. FIG. 1 also illustrates an optimal color image 16 on the substrate after removal of the tamper-evident tape (note, for purposes of the disclosure, "color" is represented by black and white or gray scale images), and an example of suboptimal adhesive residue 18 on the substrate after removal of the tamper-evident tape.

In general, the disclosed embodiments methods and systems for comparing the amount of residue transfer to a substrate when tamper-evident tape is removed. Such an approach can be selected to secure shipments and includes a visual analysis of residue transferred by tamper-evident tape to the substrate (e.g., a cargo box, pallet wrapping, other container, etc.) once the tamper-evident tape is removed. If, for example, a tamper-evident tape is designed to leave 100% color adhesive to a substrate surface, the image on the adhesive side of the tamper-evident tape and the image left by 100% deposition of adhesive on the substrate will be identical (e.g., see images 12 and 16 in FIG. 1) and no adhesive will remain affixed to the backing of the tamper-evident tape (e.g., see image 14 in FIG. 1).

Such an approach further involves establishing a defined test area on a substrate material on which a residual image has been formed by pulling of a tamper-evident tape and then dividing the area into a predefined number of units. The number of units in which a residual amount of pigment, color or other residue has been left behind on the substrate surface (e.g., see image 18 in FIG. 1) can then be counted and compared to the number of units within an area of unapplied tamper-evident tape of identical application design. The percentage of units remaining on the substrate after removal of the tamper-evident tape with color, pigment, and/or residual material can be employed as the criterion for evaluating the relative effectiveness of the tamper-evident tape and may be related to a specified performance standard by tamper-evident tape users or regulators.

Figure 2:
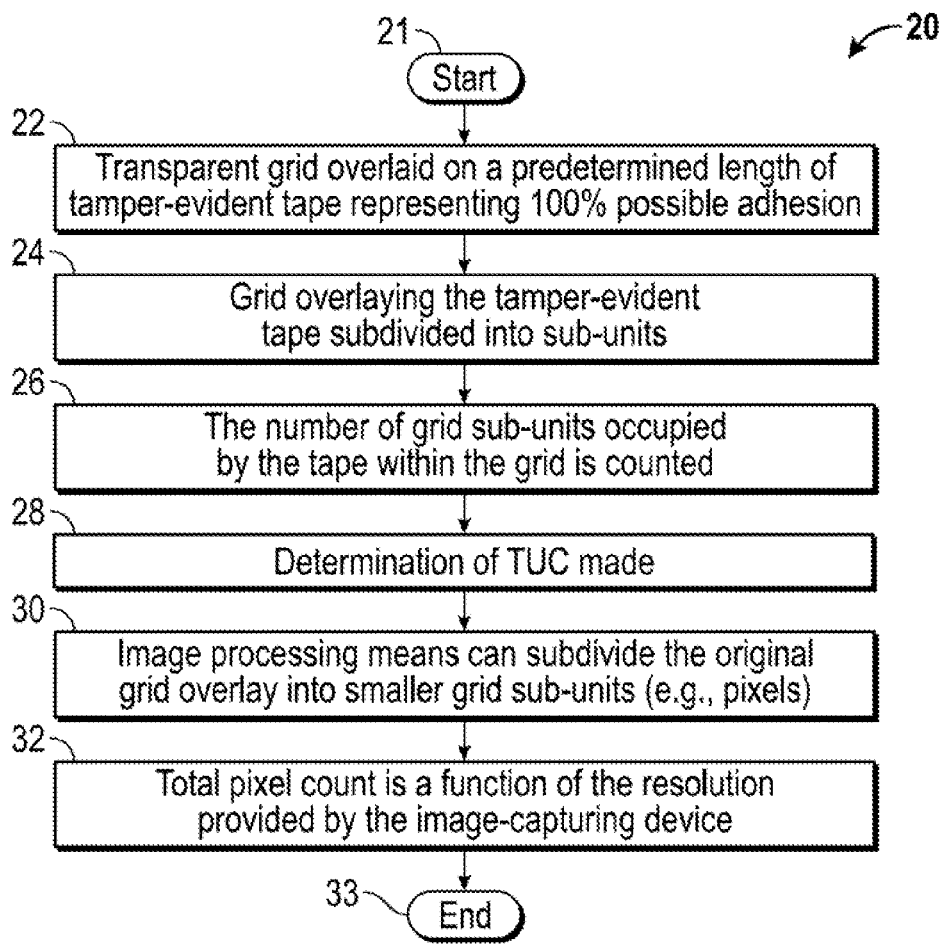
FIG. 2 illustrates a high-level flow chart depicting logical operational steps of a method for determining tamper-evident tape in accordance with the disclosed embodiments.

FIG. 2 illustrates a high-level flow chart depicting logical operational steps of a method 20 for determining tamper-evident tape in accordance with the disclosed embodiments. As indicated at block 21, the process is initiated. Thereafter, as described at block 22, a transparent grid can be overlaid on a predetermined length of tamper-evident tape representing 100% possible adhesion (i.e., a control image). Then, as shown at block 24, such grid overlaying the tamper-evident tape can be subdivided into sub-units. Thereafter, as illustrated at block 26, the number of grid sub-units occupied by the tape within the grid can be counted. The total number of grid sub-units constitutes a TUC (Tape Unit Count). Determination of the TUC can then be made, as described at block 28, via a digital capture of the tape image, wherein the image is captured through an image capturing device such as, for example, a digital camera, handheld scanner or other image processing means capable of image capture and digitization.

As indicated next at block 30, such an image processing means can subdivide the original grid overlay into smaller grid sub-units known as pixels. As indicate thereafter at block 32, the total pixel count will be generally a function of the resolution provided by the image capturing device, whereby the higher resolution capability of the image capturing device, the higher the TUC. The TUC is a value that represents 100% of the residue available for transfer from the original grid area of tamper-evident tape to be analyzed. Note that the image processing means employed can be configured in some embodiments to identify and designate color and location values for each pixel. The process can then terminate, as indicated at block 33.

Figure 3:
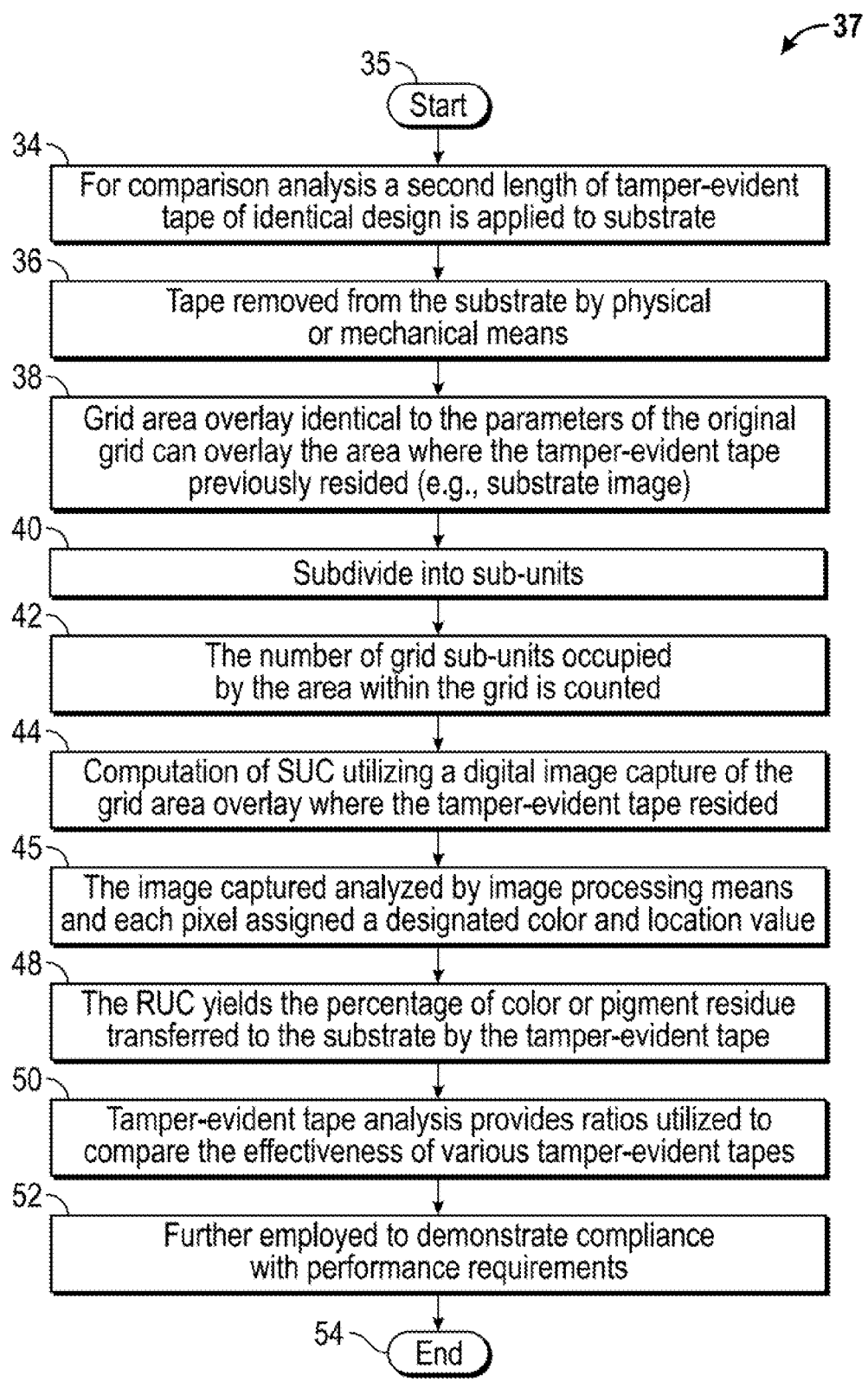
FIG. 3 illustrates a high-level flow chart depicting continued logical operational steps of the method depicted in FIG. 2, in accordance with the disclosed embodiments.

FIG. 3 illustrates a high-level flow chart depicting additional logical operational steps of a method 37 for determining tamper-evident tape in accordance with the disclosed embodiments. Note that the method 37 depicted in FIG. 3 is preferably a continuation of the method 20 shown in FIG. 2. However, method 37 may stand on its own and implemented as its own process or may be used in association or with the method 20 of FIG. 2. Additionally, as will be explained in greater detail herein, the steps or logical operations shown in FIGS. 2-3 can be implemented in the context of software. As indicated at block 35, the process begins. Then, as shown at block 34, for comparison analysis a second length of tamper-evident tape of identical design can be applied to a substrate (e.g., a cardboard shipping box). The tamper-evident tape should be firmly affixed to the substrate in accordance with the manufacturer's instructions for application. After the tamper-evident tape is affixed to the substrate in a manner indicative of complete adhesion (e.g., removal of bubbles or folds), the tape can be removed from the substrate by physical or mechanical means (e.g., pulling), as shown at block 36.

A grid area overlay identical to the parameters of the original grid can then overlay the area where the tamper-evident tape previously resided (e.g., substrate image), as depicted at block 38, and can then be subdivided into sub-units, as illustrated at block 40. The number of grid sub-units occupied by the area within the grid can then be counted, as indicated at block 42. The total value of grid sub-units constitutes the SUC (Substrate Unit Count). Computation of SUC can be performed utilizing a digital image capture of the grid area overlay where the tamper-evident tape resided, as shown at block 44. The parameters of the grid area analyzed should be identical to those of the original grid area used on the un-affixed tamper-evident tape sample.

The image captured can then be analyzed by image processing means and each pixel assigned a designated color and location value, as described at block 45. Application of the image processing means can include, for example, the incorporation of decision criteria to determine whether or not a pixel contains an image that correlates to the color and location of a pixel on the control image or substrate image.

For example, the decision criterion may correlate image/location pixel data between the control image and the substrate image produced by the removed tamper-evident tape to determine the percentage of pixels within the substrate image that match the color and location of the control image.

For tamper-evident tape designs incorporating a possible 100% deposition of adhesive residue and a single color, the SUC may be divided by the TUC to derive an RUC (Residual Unit Count). As shown at block 48, the RUC yields the percentage of color or pigment residue transferred to the substrate by the tamper-evident tape. Such a tamper-evident tape analysis can provide ratios utilized to compare the effectiveness of various tamper-evident tapes, as shown at block 50, and can be further employed to demonstrate compliance with performance requirements as indicated at block 52. For example, the criterion may be a SUT/TUC=50% or more pigment transfer requirement, if a tape product is to be procured. The process can then terminate, as indicated at block 54.

Figure 4:
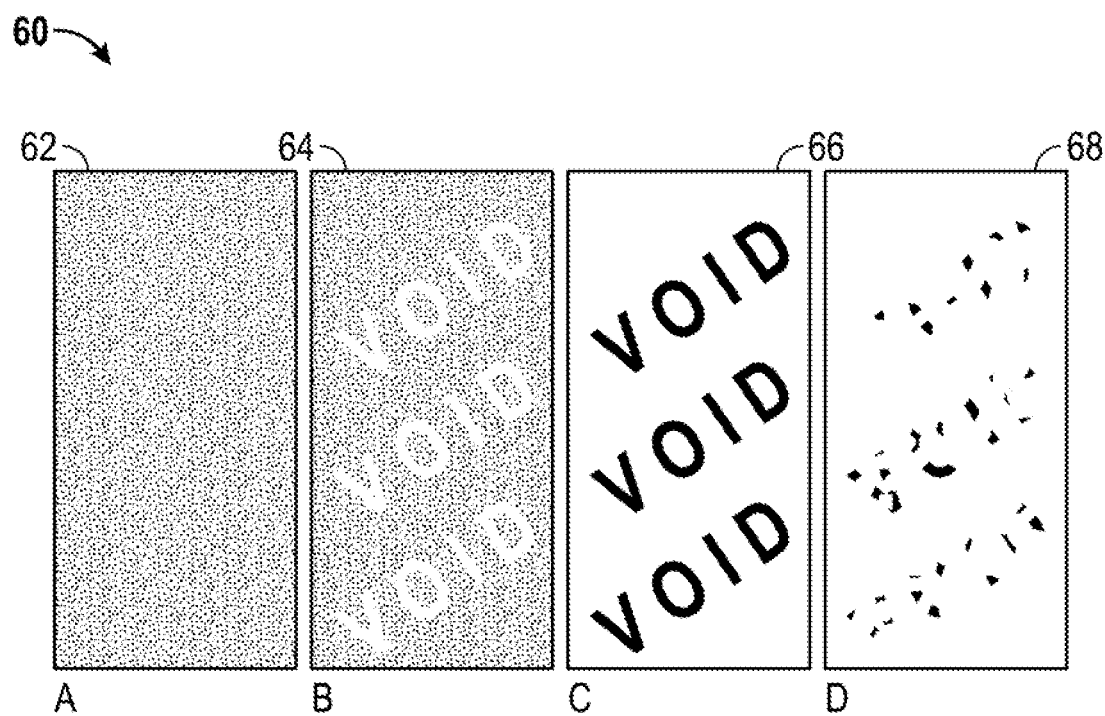
FIG. 4 illustrates a schematic diagram depicting tamper-evident tape performance variation, in accordance with an alternative embodiment.

FIG. 4 illustrates a schematic diagram depicting tamper-evident tape performance variation, in accordance with an alternative embodiment. That is, the disclosed approach can also be employed when the tamper-evident tape is specifically designed to deposit less than 100% residue. Such designs generally can incorporate the deposition of residue on the substrate in a meaningful formation such as words or a specific pattern. Tamper-evident tape of such design may require the TUC to be determined from a sample of un-affixed tamper-evident tape obtained from a source other than the application roll or an application roll of identical design.

For tamper-evident designs incorporating security features where less than 100% of adhesive is intended to remain on the substrate, a control image from which to obtain the TUC may be required to be obtained from the manufacturer. For example, a tamper-evident tape configuration 60 of the type depicted in FIG. 4 may be employed. In such a scenario, image 62 is the image of the tamper-evident tape before application, and image 64 represents the image of the tamper-evident tape backing after removal from an applied to substrate. Image 66 represents the image that would be (e.g., 100% intended adhesives) left behind on a substrate after removal of the tamper-evident tape. Image 68 represents the image of a less than amount of adhesive left behind on the substrate. For a tamper-evident tape of such design, the TUC can be obtained from image 66 and the SUC can be obtained from image 68.

It should be noted that in general, 100% of the tamper-evident tape portion to be applied to a substrate will contain adhesive properties; however, tamper-evident tape of this type of designed whereby a portion of the adhesive has a stronger affinity for the tamper-evident tape than the substrate. In such tamper-evident tape designs, a portion of the tamper-evident tape adhesive backing can be configured to remain affixed to the tamper-evident tape and not break away from the tamper-evident tape backing and remain on the substrate upon removal of the tamper-evident tape from the substrate.

In general, image 62 shown in FIG. 4 represents the original tape on substrate, and image 64 is indicative of a reverse color image on tamper-evident tape backing after removal. Note that in the drawings, "color" is represented in black and white and or gray scale. Image 66 represents the optimal color image on the substrate after tamper-evident tape removal. Finally, image 68 represents an example of sub-optimal adhesive residue after tape removal.

The disclosed approach can be utilized to determine the effectiveness of tape adhesion as a function of substrate. The adhesive properties of any tamper-evident tape are directly dependent upon the substrate of which the tamper-evident tape is adhered. Substrates used in the art include paper, cardboard, metallic, plastic, and recycled materials. The surface qualities of each type of substrate material directly affect the ability of the substrate to bond to such surface.

The disclosed approach also can be employed to determine the effectiveness of tamper-evident tape adhesive with respect to particular substrates via a visual determination of adhesive residue remaining on various substrate surfaces. For example, recycled paper packaging has a lower surface breakaway strength than standard paper packaging. TET used on some forms of recycled packaging, for example, will likely leave less adhesive on the surface when removed due to the surface of the package breaking away before the adhesive breaks from the TET backing.

The disclosed analysis approach can also be practiced whereby "color" as identified by the image processing means is not limited to the visible light spectrum within 390 nm to 750 nm wavelengths and can also include x-ray, ultra-violet, and infra-red wavelengths of light. Tamper-evident tape residue containing ultra-violet dyes and certain tape products, for example, are capable of producing x-rays when removed.

The disclosed approach can also provide the ability to identify unique tamper-evident tape of unique security designs that have been replaced with identical tape from the same manufacturer after the original tape was removed and residue cleaned off the substrate. Comparing the TUC image of the tape section to be applied with that of the SUC image on the substrate and then comparing the grid units or pixels within the TUC for incompatibility of location and color with the grid units or pixels within the SUC can accomplish such an embodiment, for example.

In some embodiments, a database of TUC values (e.g., 100% intended adhesive) left behind on a substrate after removal of the tamper-evident tape is compiled, data-processing means (e.g., computer) can be employed to analyze the adhesive residue color and location on a substrate to determine what brand/image of tamper-evident tape was originally applied, if a package is received with a full or partial image of tape adhesive due to the removal of the originally affixed tamper-evident tape.

The disclosed embodiments can be utilized with ongoing security efforts to ensure that valuable cargo is not broken into or tampered with (e.g., to prevent theft, contamination of goods, or insertion of an explosive device). To date, there has been no industry standard implemented that the details the performance requirements of tamper-evident tape to assist in securing cargo. The disclosed embodiments thus provide a technique for evaluating the effectiveness of images formed by tamper evident adhesive tapes, are marketed to promote the security of, for example, boxes, pallets, and other types of cargo.

Certain tapes provide evidence of having been tampered by leaving pigment or other residue on the substrate from which the tape was removed. The disclosed embodiments thus provide a uniform measure by which purchasers of tapes can judge the effectiveness of the tape adhesion as well as the effectiveness of pigment transfer to the substrate. In addition, the disclosed embodiments can allow any tamper-evident tape manufacturer to validate the effectiveness of their product relative to any regulatory or procurement requirements.

Figure 5A:
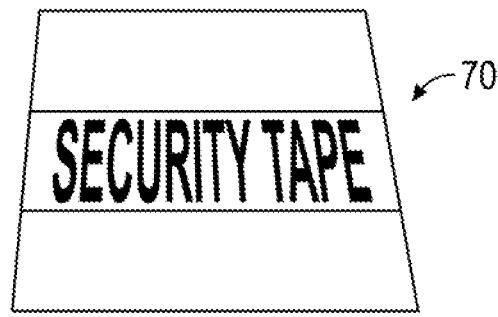
FIGS. 5(a) to 5(c) illustrate an example of a tamper evident tape deployed on a cargo box and showing signs of tampering with residue left on the cargo box in accordance with the disclosed embodiments.
Figure 5B:
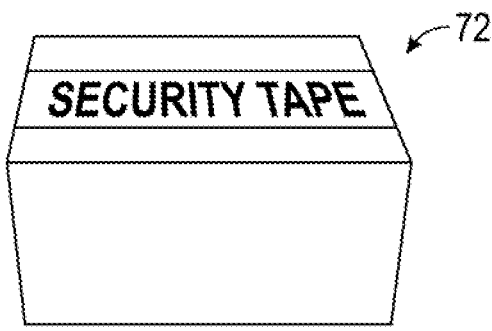
Figure 5C:
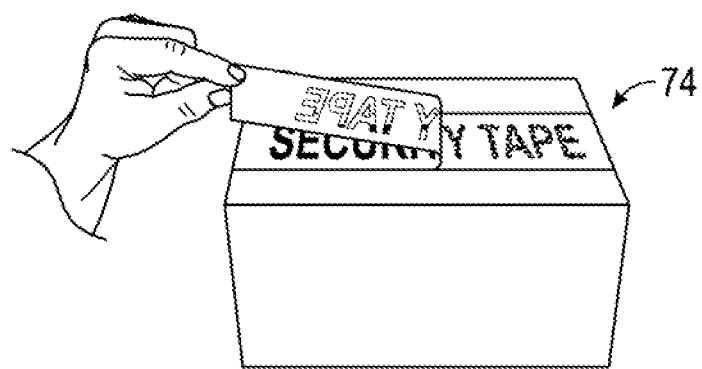

FIGS. 5(a), 5(b), and 5(c) respectively illustrate pictorial examples 70, 72, and 74 of a tamper evident tape deployed on a cargo box and showing signs of tampering with residue left on the cargo box in accordance with the disclosed embodiments.

The embodiments are described at least in part herein with reference to flowchart illustrations and/or block diagrams of methods, systems, and computer program products and data structures according to embodiments of the invention. It will be understood that each block of the illustrations, and combinations of blocks, can be implemented by computer program instructions. These computer program instructions may be provided to a processor of a general-purpose computer, special purpose computer, or other programmable data-processing apparatus to produce a machine such that the instructions, which execute via the processor of the computer or other programmable data-processing apparatus, create means for implementing the functions/acts specified in the block or blocks discussed herein such as, for example, the various instructions discussed and shown with respect to the figures herein.

These computer program instructions may also be stored in a computer-readable memory that can direct a computer or other programmable data-processing apparatus to function in a particular manner such that the instructions stored in the computer-readable memory produce an article of manufacture including instruction means which implement the function/act specified in the block or blocks.

The computer program instructions may also be loaded onto a computer or other programmable data-processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Figure 6:
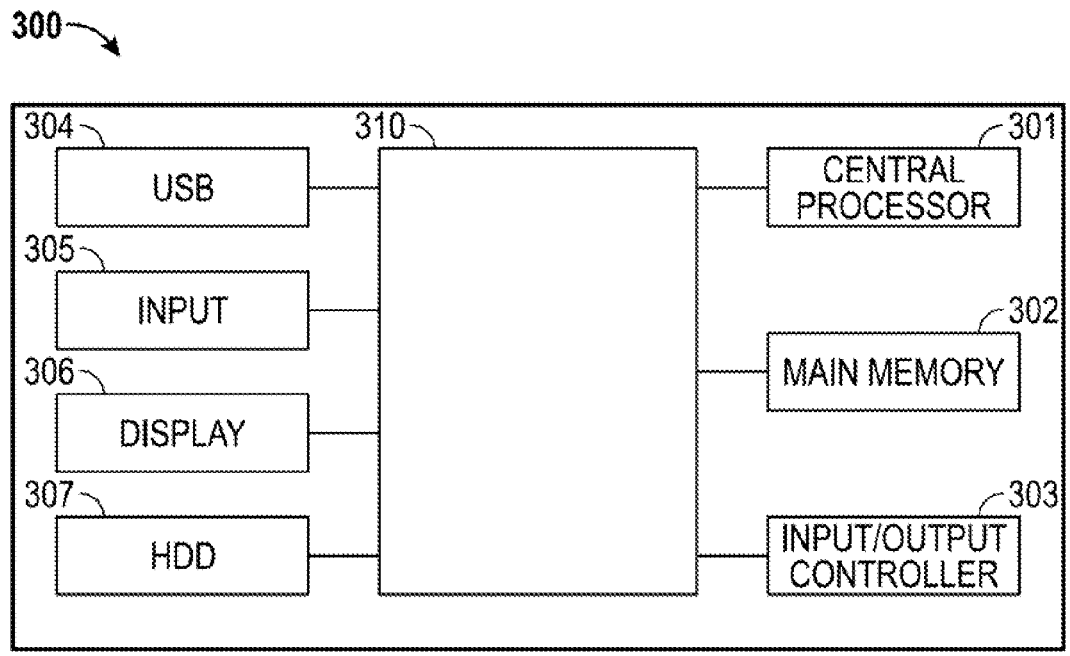
FIG. 6 illustrates a schematic view of a computer system, which can be implemented in accordance with one or more of the disclosed embodiments.
Figure 7:
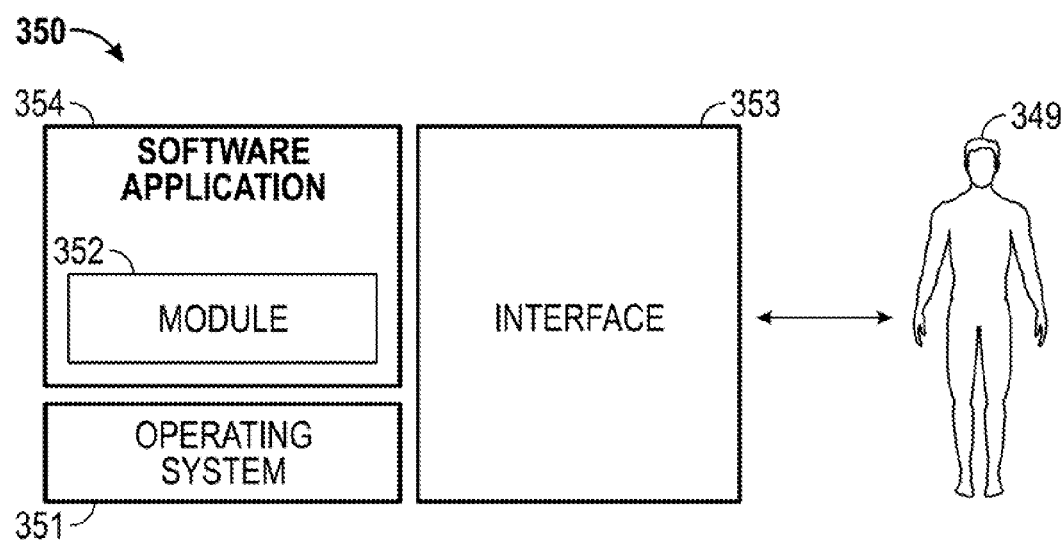
FIG. 7 illustrates a schematic view of a software system, an operating system, and a user interface, in accordance with one or more embodiments.

FIGS. 6-7 are provided as exemplary diagrams of data-processing environments in which embodiments of the present invention may be implemented. It should be appreciated that FIGS. 6-7 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

As illustrated in FIG. 6, one or more embodiments may be implemented in the context of a data-processing system 300 that can include, for example, a central processor 301 (or other processors), a main memory 302, a controller 303, and in some embodiments, a USB (Universal Serial Bus) 304 or other appropriate peripheral connection. System 300 can also include an input device 305 (e.g., a keyboard, pointing device such as a mouse, etc.), a display 306, and a HDD (Hard Disk Drive) 307 (e.g., mass storage). As illustrated, the various components of data-processing system 300 can communicate electronically through a system bus 310 or similar architecture. The system bus 310 may be, for example, a subsystem that transfers data between, for example, computer components within data-processing system 300 or to and from other data-processing devices, components, computers, etc. Data-processing system 300 may be or can include, for example, a server, a service, an engine modules, interfaces, portals, platforms, or other systems formed from computing devices.

FIG. 7 illustrates a computer software system 350, which may be employed for directing the operation of the data-processing system 300 depicted in FIG. 6. Software application 354, stored in memory 302 and/or on HDD 307, generally can include and/or can be associated with a kernel or operating system 351 and a shell or interface 353. One or more application programs, such as module(s) 352, may be "loaded" (i.e., transferred from mass storage or HDD 307 into the main memory 302) for execution by the data-processing system 300. In the example shown in FIG. 7, module 352 can be implemented as, for example, a software module or program code that performs one or more of the logical instructions or operations of, for example, the methods 20, 37 respectively shown in FIGS. 2-3 herein.

The data-processing system 300 can receive user commands and data through user interface 353 accessible by a user 349. These inputs may then be acted upon by the data-processing system 300 in accordance with instructions from operating system 351 and/or software application 354 and any software module(s) 352 thereof.

The discussion herein is thus intended to provide a brief, general description of suitable computing environments in which the system and method may be implemented. Although not required, the disclosed embodiments will be described in the general context of computer-executable instructions such as program modules being executed by a single computer. In most instances, a "module" constitutes a software application.

Generally, program modules (e.g., module 352) can include, but are not limited to, routines, subroutines, software applications, programs, objects, components, data structures, etc., that perform particular tasks or implement particular abstract data types and instructions. Moreover, those skilled in the art will appreciate that the disclosed method and system may be practiced with other computer system configurations such as, for example, hand-held devices, multi-processor systems, data networks, microprocessor-based or programmable consumer electronics, networked personal computers, mini-computers, mainframe computers, servers, and the like.

Note that the term module as utilized herein may refer to a collection of routines and data structures that perform a particular task or implements a particular abstract data type. Modules may be composed of two parts: an interface, which lists the constants, data types, variable, and routines that can be accessed by other modules or routines, and an implementation, which is typically private (accessible only to that module) and which includes source code that actually implements the routines in the module. The term module may also simply refer to an application such as a computer program designed to assist in the performance of a specific task such as word processing, accounting, inventory management, etc.

The interface 353 (e.g., a graphical user interface) can serve to display results, whereupon a user may supply additional inputs or terminate a particular session. In some embodiments, operating system 351 and interface 353 can be implemented in the context of a "windows" system. It can be appreciated, of course, that other types of systems are possible. For example, rather than a traditional "windows" system, other operation systems such as, for example, a real time operating system (RTOS) more commonly employed in wireless systems may also be employed with respect to operating system 351 and interface 353.

FIGS. 6-7 are thus intended as examples and not as architectural limitations of disclosed embodiments. Additionally, such embodiments are not limited to any particular application or computing or data processing environment. Instead, those skilled in the art will appreciate that the disclosed approach may be advantageously applied to a variety of systems and application software. Moreover, the disclosed embodiments can be embodied on a variety of different computing platforms, including Macintosh, Unix, Linux, and the like.

Based on the foregoing, it can be appreciated that a number of embodiments, alternative and preferred, are disclosed herein. For example, in a preferred embodiment, a method can be implemented for measuring the effectiveness of pigment transfer in a tamper-evident tape. Such a method can include, for example, the steps or logical operations of establishing a test area on a substrate upon which a residual image is formed by pulling a tamper-evident tape; dividing the test area into a predefined number of units; counting a number of units in which a residual is left behind on a surface of the substrate; and comparing the number of units to a number of units within an area of un-applied tamper-evident tape of identical application design such that a percentage of units remaining on the substrate after removal of the tamper-evident tape with the residual comprises a criterion for evaluating a relative effectiveness of the tamper-evident tape.

In some embodiments, the number units may constitute pixels. In other embodiments, the aforementioned residual may be a color. In still other embodiments, the aforementioned color can include, for example, one or more of visible spectrum light, x-ray wavelength, ultra-violet wavelength, infrared wavelength, etc. In yet other embodiments, the aforementioned residual may be a pigment. In still other embodiments, the aforementioned residual can be a residue left by the tamper-evident tape.

In another embodiment, a system can be provided for measuring the effectiveness of pigment transfer in a tamper-evident tape. Such a system can include, for example, a processor, a data bus coupled to the processor, and a computer-usable medium embodying computer program code, the computer-usable medium being coupled to the data bus. Such computer program code can include, for example, instructions executable by the processor and configured for dividing a test area on a substrate into a predefined number of units, wherein a residual image is left behind on the substrate by a tamper-evidence tape with respect to the test area, counting a number of units in which a residual is left behind on a surface of the substrate, and comparing the number of units to a number of units within an area of un-applied tamper-evident tape of identical application design such that a percentage of units remaining on the substrate after removal of the tamper-evident tape with the residual comprises a criterion for evaluating a relative effectiveness of the tamper-evident tape.

In another embodiment, a processor-readable medium storing computer code representing instructions to cause a process for measuring the effectiveness of pigment transfer in a tamper-evident tape can be implemented. Such computer code can include code to, for example, divide a test area on a substrate into a predefined number of units, wherein the test area is established on the substrate upon which a residual image is formed by pulling a tamper-evident tape, count a number of units in which a residual is left behind on a surface of the substrate, and compare the number of units to a number of units within an area of un-applied tamper-evident tape of identical application design such that a percentage of units remaining on the substrate after removal of the tamper-evident tape with the residual comprises a criterion for evaluating a relative effectiveness of the tamper-evident tape.

In another embodiment, a method for establishing a standard of security can be implemented. Such a method can include the steps or logical operations of, for example, analyzing a pattern left behind on a surface by a tamper-evident tape; and automatically comparing the pattern and pixels thereof to images of other patterns left behind by various tamper-evident tapes across a variety of surfaces to derive performance standards with respect to tamper-evident tapes utilized in security applications. In yet another embodiment, a step or logical operation can be implemented for determining particular ratios for use in comparing the effectiveness of the various tamper-evident tapes.

Note that throughout the following discussion, numerous references may be made regarding servers, services, engines, modules, interfaces, portals, platforms, or other systems formed from computing devices. It should be appreciated that the use of such terms are deemed to represent one or more computing devices having at least one processor configured to or programmed to execute software instructions stored on a computer readable tangible, non-transitory medium. For example, a server can include one or more computers operating as a web server, database server, or other type of computer server in a manner to fulfill described roles, responsibilities, or functions. Within the context of this document, the disclosed printers, assemblies, or space craft are also deemed to comprise computing devices having a processor and a non-transitory memory storing instructions executable by the processor that cause the device to control, manage, or otherwise manipulate the features of the assemblies.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A method for measuring the effectiveness of tamper-evident tape, said method comprising:

establishing a test area on a substrate surface upon which a residual image is formed by pulling a tamper-evident tape;

dividing said test area into a predefined number of units;

counting a number of units in which a residual is left behind on said substrate surface; and comparing said number of units to a number of units within an area of un-applied tamper-evident tape of identical application design to determine a percentage of units remaining on said substrate surface after removal of said tamper-evident tape with said residual, the percentage comprises a criterion for evaluating a relative effectiveness of said tamper-evident tape.

2. The method of claim 1 wherein said number units comprises pixels.

3. The method of claim 1 where said residual comprises a colored residue.

4. The method of claim 3 wherein said colored residue includes at least one of visible spectrum light, x-ray wavelength, ultra-violet wavelength, or infrared wavelength.

5. The method of claim 1 wherein said residual comprises a pigment.

6. The method of claim 5 wherein said residual comprises pigmented residue left by said tamper-evident tape.

7. A system for measuring the effectiveness of pigment transfer in a tamper-evident tape, operative to read a computer-usable medium embodying a program of instruction that when executed by the system cause said system to:
   divide a test area on a substrate into a predefined number of units, wherein a residual image is left behind on said substrate by a tamper-evidence tape with respect to said test area;
   count a number of units in which a residual is left behind on a surface of said substrate; and
   compare said number of units to a number of units within an area of un-applied tamper-evident tape of identical application design so a percentage of units remaining on said substrate after removal of said tamper-evident tape with said residual comprises a criterion for evaluating a relative effectiveness of said tamper-evident tape.

8. The system of claim 7 wherein said number units comprises pixels.

9. The system of claim 7 wherein said residual comprises a color.

10. The system of claim 9 wherein said color includes at least one of: visible spectrum light, x-ray wavelength, ultra-violet wavelength, or infrared wavelength.

11. The system of claim 7 wherein said residual comprises a pigment.

12. A non-transitory processor-readable medium storing instructions that are operable to cause a computer to process for measuring the effectiveness of pigment transfer in a tamper-evident tape, said computer code further comprising code to:
   divide a test area on a substrate into a predefined number of units, wherein said test area is established on said substrate upon which a residual image is formed by pulling a tamper-evident tape;
   count a number of units in which a residual is left behind on a surface of said substrate; and
   compare said number of units to a number of units within an area of un-applied tamper-evident tape of identical application design such that a percentage of units remaining on said substrate after removal of said tamper-evident tape with said residual comprises a criterion for evaluating a relative effectiveness of said tamper-evident tape.

13. The non-transitory processor-readable medium of claim 12 wherein said number units comprises pixels.

14. The non-transitory processor-readable medium of claim 12 where said residual comprises a color.

15. The non-transitory processor-readable medium of claim 14 wherein said color includes at least one of: visible spectrum light, x-ray wavelength, ultra-violet wavelength, or infrared wavelength.

16. The non-transitory processor-readable medium of claim 12 wherein said residual comprises a pigment.

17. The non-transitory processor-readable medium of claim 12 wherein said residual comprises a residue left by said tamper-evident tape.

* * * * *